United States Patent
Broeders et al.

(10) Patent No.: US 6,455,740 B1
(45) Date of Patent: Sep. 24, 2002

(54) PROCESS TO SEPARATE A GROUP 8-10 METAL/PHOSPHITE LIGAND COMPLEX FROM AN ORGANIC LIQUID

(75) Inventors: Nicolaas L. H. L. Broeders, Wagenberg; Onko J. Gelling, Stein; Hendrik F. Martens, Houten; Klaas Timmer, Bilthoven; Harmen A. Meinema, Leusden, all of (NL)

(73) Assignee: DSM N.V., Heerlen (NL)

(*) Notice: Subject to any disclaimer, the term of this patent is extended or adjusted under 35 U.S.C. 154(b) by 0 days.

(21) Appl. No.: 09/500,083

(22) Filed: Feb. 8, 2000

Related U.S. Application Data

(63) Continuation of application No. PCT/NL98/00433, filed on Jul. 29, 1998.
(60) Provisional application No. 60/059,726, filed on Sep. 23, 1997.

(30) Foreign Application Priority Data

Aug. 8, 1997 (EP) .............................. 97202452

(51) Int. Cl.⁷ .................. C07C 45/50; C07F 17/02; B01J 31/00
(52) U.S. Cl. .................. 568/454; 568/451; 556/18; 502/168; 502/166; 502/161; 502/162; 502/167
(58) Field of Search ................ 568/454, 451; 556/18; 502/168, 166, 161, 162, 167

(56) References Cited

U.S. PATENT DOCUMENTS

| | | | |
|---|---|---|---|
| 4,668,651 A | 5/1987 | Billig et al. | |
| 4,748,261 A | 5/1988 | Billig et al. | |
| 4,769,498 A | 9/1988 | Billig et al. | |
| 4,834,869 A | * 5/1989 | Angevine et al. | 208/213 |
| 5,114,473 A | 5/1992 | Abatjoglou et al. | |
| 5,208,194 A | 5/1993 | Pitchai et al. | 502/12 |
| 5,235,113 A | 8/1993 | Sato et al. | |
| 5,927,950 A | 7/1999 | Juvenal | |

FOREIGN PATENT DOCUMENTS

| | | |
|---|---|---|
| EP | 0186409 A2 | 7/1986 |
| EP | 0355837 A2 | 2/1990 |
| EP | 0 518 241 A2 | 12/1992 |
| EP | 0 556 681 A1 | 8/1993 |
| EP | 0 712 828 A1 | 5/1996 |
| WO | WO 95/18089 | 7/1995 |

OTHER PUBLICATIONS

Cuny, et al., "Practical, High–Yield, Regioselective, Rhodium–Catalyzed Hydroformylation of Functionalized α–Olefins", J. Am. Chem. Soc. 1993 115, pp. 2066–2068.

Hovorka, et al., "Highly Selective Oxidative . . . 1,1'–Binaphthalene–2,2'–Diols", Tetrahedron Letters, vol. 31, No. 3, (1990) pp. 413–416.

Miller, et al., "The Reactivity of the Methyl Group in 2–Methyl–3–nitronphthalene", vol. 76, pp. 196–297 (1989).

K.G. Allum, et al. "Supported Transition Metal Complexes", Journal of Organometallic Chemistry, 87 1975, pp. 203–216.

K.D. Behringer, et al., "Immobilization of Carbonylnickel Complexes: A Solid–State NMR Study", Inorganic Chemistry 35, 1996 pp. 1814–1819.

Journal of American Chemical Society, 1993, 115, 2066–2068.

* cited by examiner

Primary Examiner—Sreeni Padmanabhan
(74) Attorney, Agent, or Firm—Pillsbury Winthrop LLP

(57) ABSTRACT

Process to separate a group 8–10 metal/phosphite ligand complex from an organic liquid mixture, wherein the following steps are performed (1) contacting the organic liquid with a support having bonded thereto an organophosphine ligand and separating the organic mixture which is poor in group 8–10 metal/phosphite ligand complex, (2) contacting the thus obtained loaded support with an organic solvent and carbon monoxide and separating the thus obtained organic solvent rich in group 8–10 metal/phosphite ligand complex, and (3) reusing the support obtained in step (2) in step (1).

12 Claims, No Drawings

PROCESS TO SEPARATE A GROUP 8-10 METAL/PHOSPHITE LIGAND COMPLEX FROM AN ORGANIC LIQUID

This is a Continuation of: International Appln. No. PCT/NL98/00433 filed Jul. 29, 1998 which designated the U.S.

This application claims the benefit of U.S. Provisional Application No. 60/059,726, filed Sep. 23, 1997.

The invention relates to a process to separate a group 8–10 metal/phosphite ligand complex from an organic liquid mixture.

A process to recover rhodium from an organic liquid derived from a hydroformylation process is described in EP-A-355837. In this known process, the rhodium containing liquid is firstly contacted with an ion-exchange resin having bonded ionically thereto an organophosphorous ligand (adsorption of rhodium). Subsequently rhodium is desorped from the thus obtained support by treating the support with a liquid in which the different or preferably the corresponding organophosphorous ligand is dissolved. According to this disclosure the rhodium concentration in the liquid is preferably low, i.e. less than 20 ppm rhodium.

It has been found that, when a phosphite ligand is present in the organic mixture, the phosphite ligand is not recovered by the process according to EP-A-355837. Furthermore the efficiency of the process is low, resulting in that under practical conditions only mixtures can be treated having a low concentration of the group 8–10 metal. According to a preferred embodiment of the process as described in EP-A-355837 the desorption is performed starting with organic mixtures containing dissolved organophosphorus ligands having an ionic moiety. Thus a group 8–10 metal/organophosphorus ligand complex, in which the ligand has an ionic moiety, is at the end obtained. It is however advantageous to directly use the resulting complex in a hydroformylation reaction. Because ligands having ionic moieties are normally used for water soluble catalyst systems and because phosphite ligands are unstable in the presence of water one skilled in the art would not be motivated to use the teachings of EP-A-355837 for the separation of a group 8–10 metal/phosphite ligand complex from an organic liquid mixture.

The object of the invention is a process to separate a group 8–10 metal/phosphite ligand complex from an organic liquid and in which the complex can be recovered and simply reused as a catalyst.

The object is achieved in that the following steps are performed (1) contacting the organic liquid with a support having bonded thereto an organophosphine ligand and separating the organic mixture which is poor in group 8–10 metal/phosphite ligand complex, (2) contacting the thus obtained loaded support with an organic solvent and carbon monoxide and separating the thus obtained organic solvent rich in group 8–10 metal/phosphite ligand complex, and (3) reusing the support obtained in step (2) in step (1).

It has been found that with the process according to the invention group 8–10 metal/phosphite ligand complex can be separated from the organic liquid with a high yield in step (1) and recovered for further use in step (2) in its original, catalytically active form. A further advantage of the process according to the invention is that the group 8–10 metal may be present in the liquid in high concentrations. Another advantage is that the process of the invention regenerates the support for direct reuse.

The use of a group 8–10 metal of the Periodic System of the Elements (New IUPAC notation; Handbook of Chemistry and Physics, 70th edition, CRC Press, 1989–1990) such as rhodium or iridium as part of a homogeneous catalyst system is well known in the art. Typical examples of such processes include the hydroformylation of an unsaturated compound with carbon monoxide and hydrogen to give an aldehyde, the hydrocyanation of unsaturated compounds, the hydrogenation of olefinic compounds and the polymerisation of olefins. In such a process, the group 8–10 metal catalyst generally is stabilized with a ligand.

The organic liquid to be treated in the process according to the invention is for example obtained in a hydroformylation process in which a homogeneous catalyst system is used comprising the group 8–10 metal/phosphite ligand complex. It has been found that the group 8–10 metal/phosphite ligand complex can advantageously be separated from the product stream of such process.

A problem in such hydroformylation processes is the possible accumulation of high boiling compounds in the recirculating catalyst stream. It is therefor necessary to separate the high boiling compounds by means of a purge. For a commercially interesting process it is necessary to recover the catalyst system comprising the group 8–10 metal/phosphite ligand complex from such a purge stream. This is especially advantageous when using valuable group 8–10 metal/phosphite ligand complexes such as for example described in WO-A-9518089.

The group 8–10 metal complex to be recovered by the process according to the invention is present as a soluble group 8–10 metal complex. Without wishing to be bound to any particular theory, it is believed that in step (1) of the process according to the invention the group 8–10 metal complex forms a coordination complex with the organophosphine ligand which is bonded on the support, whereby at least one ligand of the complex is displaced for the organophosphine ligand. Accordingly, it is preferred that at least one exchangeable ligand (L) is present in the complex to be recovered.

Examples of suitable group 8–10 metals are nickel, cobalt, ruthenium, rhodium, palladium, platinum, osmium and iridium. The invention is especially directed to recover rhodium because of its high price.

The mechanism of the first step can, for example for rhodium, be represented as follows:

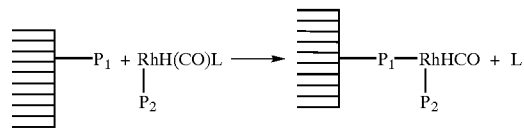

in which $P_1$ is the immobilized organophosphine ligand and $P_2$ is the phosphite ligand and L is the exchangeable ligand.

L is for example CO, a phosphine, phosphite, phosphinite, phosphonite, olefin, nitrile, β-diketone or a β-ketoester. L is preferably CO.

The temperature applied during the adsorption of the rhodium complex is generally between 0° C. and 150° C., preferably between 15 and 80° C. and most preferably between 20 and 30° C. The temperature is preferably relatively low to minimize degradation of the support and the immobilized complex.

The pressure applied during the adsorption is generally not critical and will in practice be between atmospheric pressure and pressures high enough to overcome any pressure drop in the process equipment.

The adsorption of the group 8–10 metal complex on the support having bonded thereto organo-phosphine ligands can simply be performed by contacting the liquid containing the rhodium complex and the support batchwise, semi-continuously or continuously. When performing the contacting batchwise, an appropriate amount of the support is stirred with the liquid to be treated until a sufficient degree of adsorption is achieved, for example during for about 0,5 to 6 hours. Subsequently, the loaded support is separated from the treated organic liquid with any known solid-liquid separation method. Examples of suitable separation methods are filtration and centrifugation. Preferably, the contacting is performed continuously by passing the liquid to be treated continuously over one or more beds of the support, whereby the separation of the rhodium loaded support from the liquid is inherently facilitated. The bed may be a fixed bed or a liquid fluidized bed. Preferably a fixed bed is used.

The group 8–10 metal complex can subsequently be removed from the loaded support by contacting the loaded support with a suitable organic solvent and carbon monoxide to desorb at least a part of the adsorbed group 8–10 metal phosphite complex from the support (step (2)). Preferably also some hydrogen is present. The desorption of the group 8–10 metal complex is performed in the presence of an organic solvent in which the desorbed group 8–10 metal phosphite complex is soluble. Without wishing to be bound to any particular theory, it is believed that at least the organophosphine ligand of the support is displaced for the carbon monoxid used in step (2), when the group 8–10 metal phosphite complex dissolves in the organic solvent. The temperature applied during the desorption is generally between 0° C. and 150° C., more preferably between 60° C. and 120° C.

Suitable solvents are aromatic solvents, for example benzene, toluene, xylene; hydrocarbon solvents, for example heptane, octane, nonane; functionalized solvents, for example ethers, for example methyl tert-butylether or esters, for example ethylacetate. Most prefered solvents are, starting compounds, products and by-products of the (hydroformylation) reaction.

Preferably step (2) is performed at a CO or CO/$H_2$ partial pressure of between 0.1–10 MPa. More preferred step (2) is performed by contacting the loaded support with the organic solvent, which is saturated with CO or CO/$H_2$. Saturation is preferably performed at a pressure of between 2–15 MPa. The molar ratio CO and $H_2$ is preferably between 10:1 and 1:10 and more preferably about 1:1.

The mechanism of the desorption step (2) can, for example for rhodium, be represented as follows:

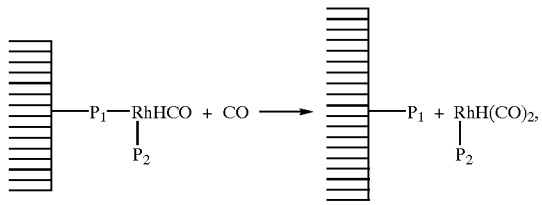

Step (2) can be performed batchwise, semi-continuously or continuously. When performing step (2) batchwise, the loaded support is stirred with an appropriate amount of the organic solvent in the presence of carbon monoxide until a sufficient degree of desorption is achieved. Contacting time may be for example 0,5 to 6 hours and preferably between 1 and 3. Subsequently, the support is separated from the organic solvent containing the desorbed group 8–10 metal/phosphite complex with any known solid-liquid separation method. Preferably, the desorption is performed continuously over a fixed or liquid fluidized bed of the loaded support. Preferably a fixed bed is used.

The process according to the invention can be carried out batchwise or, preferably, in a continuous process. In a commercial process the reaction is preferably carried out in a continuous mode. When such a type of operation is utilized, at least two columns containing the support are operated parallel, in order to perform step (1) to (3) simultaneously. For example, the liquid mixture to be treated is continuously passed through a first column. After utilizing this support for a predetermined period of time, the flow of the liquid mixture is passed through a second column in order to continue step (1). The first column containing loaded support is subjected to the desorption step (2). After desorbing the rhodium/phosphite complex from the support for a predetermined period of time, the first column can be reused for a subsequent adsorption step (step (3)). This ad- and desorption cycle can be repeated for all the columns resulting in a continuous removal and retrieval of the rhodium/phosphite complex from the organic liquid.

The process according to the invention will be described in more detail for the following preferred embodiments. It shall be evident that the below stated conditions will also be applicable for the above described starting mixtures in a manner clear to one skilled in the art.

A suitable organophosphine ligand, which is bonded onto the support, is in principle any organophosphine ligand which is able to coordinate with the rhodium complex. These organophosphine ligands are well known in the art. A preferred class of organophosphine ligands are monodentate and bidentate organic phosphines. The most preferred organophosphine ligands are monodentate phosphines.

Preferably the support having bonded thereto an organophosphine ligand can be represented with a structure according the following general formula (1) or (2):

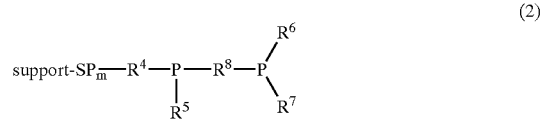

in which m=0 or 1; SP is a linking group; $R^2$, $R^3$, $R^5$, $R^6$ and $R^7$ are the same or different optionally substituted hydrocarbon groups containing 1 to 30 carbon atoms and $R^1$, $R^4$ and $R^8$ are divalent organic bridging groups having 1 to 30 carbon atoms.

The hydrocarbon group of the groups $R^2$, $R^3$, $R^5$, $R^6$ and $R^7$ are preferably an alkyl, aryl, alkaryl, aralkyl or cycloalkyl group. The hydrocarbon group preferably contains from 1 to 18 carbon atoms and more preferably 1 to 12 carbon atoms. Examples of possible hydrocarbon groups are methyl, ethyl, propyl, butyl, hexyl, cyclohexyl and phenyl.

Preferably, at least one hydrocarbon group of $R^1$, $R^2$ and $R^3$ in formula (1) and at least one hydrocarbon group of $R^5$, $R^6$ and $R^7$ in formula (2) is a phenyl group. More preferably, at least two hydrocarbon groups, and most preferably all the hydrocarbon groups, of $R^1$, $R^2$ and $R^3$ in formula (1) and $R^5$, $R^6$ and $R^7$ in formula (2) are phenyl groups. These hydrocarbon groups may contain one or more substituents. Examples of suitable substituents are alkyl groups, preferably of 1 to 5 carbon atoms, alkoxy groups, halogen atoms, hydroxy, cyano, nitro and amino groups.

Divalent groups $R^1$ and $R^4$ are organic bridging groups containing 1–30 carbon atoms and optionally containing heteroatoms, for example O, N or S. Preferably $R^1$ and $R^4$ are alkylene, arylene, or combinations of an alkylene and an arylene group.

Examples of suitable divalent groups $R^8$ are hydrocarbon groups or hydrocarbon groups whereby two hydrocarbon groups are bridged with an oxygen-, sulphur or nitrogen atom. The hydrocarbon group preferably contains 1 to 16 carbon atoms and more preferably 1 to 12 carbon atoms. Most preferably, $R^8$ is a divalent alkylene radical containing from 2 to 8 carbon atoms, for example ethylene, propylene or butylene.

The linking group SP, is a group which links the phosphine ligand to the support. If m=o a direct covalent bond is present between the ligand and the support, as for example when triphenyl phosphine is bonded to a polystyrene support as is commercially available from Strem Chemicals. The linking group can for example be ionic in nature, as for example described in the afore mentioned EP-A-355837. Preferably the SP group is a divalent covalently bonded group. If a silica support is used the SP-group is preferably a —Si(R')(R")-group, in-which R' and/or R" can be an alkyl, alkoxy, aryl or aryloxy group and/or R' and/or R" is a covalent bond to the silica support. Examples for R' or R" are methyl, ethyl, isopropyl, isobutyl, butyl, phenyl, methoxy, ethoxy, phenoxy groups.

Preferably monodentate phosphines according to formula (1) are used. Specific examples of the monodentate organophosphine ligand to be used for the organophosphine ligand in the present invention includes triphenylphosphine, tri-p-tolylphosphine, tri-o-tolylphosphine, tri-o-methoxyphenylphosphine, tri-o-chlorophenylphosphine, diphenylisopropylphosphine and diphenylcyclohexylphosphine. The most preferred monodentate phosphine is triphenylphosphine.

The support is, for example, (a) a solid support; (b) an insoluble polymer obtained by polymerisation of a suitable monomer or mixture of monomers and subsequent cross-linking as appropriate; (c) or a soluble polymer on an insoluble support. Examples of suitable polymers are polystyrene, polyethylene, polyvinylchloride, polyvinyl pyridine, polyacrylonitrile and polyacrylates. Suitable cross-linking agents are divinylbenzene, butadiene and diallyl phtalate. The solid support is preferably an inorganic support. Examples of suitable solid inorganic support are silica, polysiloxanes, sand, glass, glass fibres, alumina, zirconia, titania and activated carbon. An especially useful inorganic support is silica.

The supported organophosphine ligands may be prepared using a variety of methods known in the art. The silica supported monodentate phosphine ligands can be prepared by means of procedures as described in Journal of Organometallic Chemistry/87, 1975, page, 203–216 and in Inorganic Chem., 35 (1996) 1814–1819 and as described in the there mentioned references. In addition to the here described methods it is preferred to react all of the non-reacted hydroxy-groups of the silica support with a reactive compound (so-called end-copping) in order to prevent that "free" hydroxy groups are present on the support which may negativelly influence the performance of the process according to the invention. Examples of these reactive compounds are ethoxy trimethyl silane or phenoxy trimethyl silane.

The amount of organophosphine ligand on the support is not critical and is generally between 0.01 and 10 mmol P/g support, preferably between 0.05 and 0.5 mmol P/g support.

It has been found that the process according to the invention can advantageously be used for recovering a rhodium/phosphite complex from an organic liquid containing also high boiling hydroformylation compounds. Such mixtures hereinafter can be obtained in the high boiling purge of a commercial hydroformylation process.

It has been found that with the process of the invention the rhodium/phosphite complex can be recovered in its original active form with a high yield. The recovery of the phosphite ligand is advantageous because of the relatively high cost price of these phosphite compounds. Another advantage of the process according to the invention is that the ligand degradation products of, especially multidentate, phosphite ligands do not adsorb to the support in step (1). This is advantageous because the ligand degradation products will be also separated from the rhodium/phosphite complex by this process.

The high boiler purge is generally removed continuously or intermittently from the hydroformylation system. The purge may be removed either directly from the reactor or, for example, from some point in the catalyst recycle stream.

The invention is therefor also directed to a process for the separation of a rhodium/multidentate phosphite ligand complex catalyst from an organic mixture comprising high boiling hydroformylation compounds.

The concentration of the rhodium complex in the liquid to be treated is not critical. In a hydroformylation high boiler purge, the concentration will generally be higher than 100 ppm rhodium and lower than 2000 ppm rhodium. Preferably, the rhodium concentration is higher than 200 ppm and lower than 1200 ppm. More preferably, the rhodium concentration is equal to or higher than 300 ppm and equal to or lower than 800 ppm.

The concentration of the high boiling compounds in the high boiler hydroformylation mixture may vary from 10–95 wt. %. Preferably, the concentration is between 20–60 wt. %.

The high boiler hydroformylation mixture containing the hydroformylation catalyst and high boiling compounds will generally comprise also 40–80 wt. % of the aldehyde product and 1–5 wt. % ligand degradation products.

After having performed the adsorption step (1), the treated liquid containing the high boiling hydroformylation compounds can be disposed of.

The high boiler purge is preferably removed from a hydroformylation system for the preparation of a linear (or terminal) aldehyde obtainable by hydroformylation of internally unsaturated olefins substituted with one or more functional groups according to formula (3):

$$CH_3—CR^9=CR^{10}—R^{11} \qquad (3)$$

where $R^9$ and $R^{10}$ are a hydrocarbon group or preferably hydrogen and $R^{11}$ is a cyanide group or a hydrocarbon group, whether or not substituted with one or more functional groups which contain a hetero atom, for example oxygen, sulphur, nitrogen or phosphorus. Preferably, use is made of internally unsaturated olefins having between 4 and 20 carbon atoms according to formula (3), where $R^9$ and $R^{10}$ are hydrogen.

Examples of internally unsaturated olefins having between 4 and 20 carbon atoms according to formula (3), where $R^9$ and $R^{10}$ are hydrogen, are 2-pentene nitrile, 3-pentene nitrile, 3-pentenoic acid and $C_1$–$C_6$-alkyl ester of 3-pentenoic acid. These resulting aldehyde hydroformylation products, in particular methyl-5-formylvalerate, are intermediate products in the preparation of ε-caprolactam or adipic acid, which are in turn raw materials for the preparation of nylon-6 and nylon-6,6, respectively. Examples of $C_1$–$C_6$-alkyl-3-pentenoate esters are methyl-, ethyl-, propyl-, isopropyl-, tert-butyl-, pentyl- and cyclohexyl-3-pentenoate. Preferably, use is made of methyl- and ethyl-3-pentenoate, because these compounds are readily obtainable. 3-pentene nitrile, 3-pentenoic acid and $C_1$–$C_6$-alkylesters of pentenoic acid may be present in the reaction mixture as a mixture which also comprises 2- and 4-pentenenitrile, 2- and 4-pentenoic acid and $C_1$–$C_6$-alkylesters of 2- and 4-pentenoic acid, respectively.

The multidentate phosphite ligand of the rhodium complex to be recovered preferably has the following general structure:

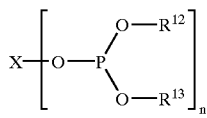

(4)

where n is 2–6, X is an n-valent organic bridging group and $R^{12}$ and $R^{13}$ are independently two organic monovalent aryl groups and/or one divalent diaryl group.

$R^{12}$ and $R^{13}$ are preferably monovalent organic groups with 1 to 20 carbon atoms or $R^{12}$ and $R^{13}$ form together one divalent organic group having 6 to 30 carbon atoms. Most preferably, $R^{12}$ and $R^{13}$ are monovalent aryl groups having 6 to 14 carbon atoms. The different $R^{12}$ and $R^{13}$ groups in the ligand may be different. For example in the same ligand some groups $R^{12}$ and $R^{13}$ may be one divalent group while other groups $R^{12}$ and $R^{13}$ are monovalent groups.

X is preferably an organic group having between 1 and 40 carbon atoms, and more preferably between 6 and 30 carbon atoms. An example of a ligand having a tetravalent organic group is a ligand having a bridging group corresponding to pentaerythritol. Bidentate ligands, having a bivalent bridging group, are most frequently mentioned in the patent literature.

Examples of such phosphite ligands are described in U.S. Pat. No. 4,748,261, EP-A-556681 and EP-A-518241.

When internally ethylenically unsaturated organic compounds, for example 2-butene or 3-pentenoate, are used as a starting material to prepare terminal aldehydes, use is preferably made of a multidentate phosphite ligand that can form a chelate-type complex with the rhodium in the reaction zone. A chelate-type complex is understood to mean that (substantially) at least two phosphorus P atoms of a ligand molecule form a coordinated bond with one rhodium atom/ion. A non-chelate-type complex is understood to mean that only one phosphorus P atom of a ligand molecule forms a coordinated bond with one rhodium atom/ion. The choice of bridging group X of the ligand will determine whether a chelate-type complex can be formed in the reaction zone. Examples of bridging groups that result in a ligand that can form a chelate-type bridging group are for example described in WO-A-9518089.

A preferred ligand for use in the process according to the invention has a 2,2'-dihydroxy-1,1'-binaphthalene bridging group, which bridging group is preferably substituted at the 3 and 3' positions. This ligand can be represented by the following general formula:

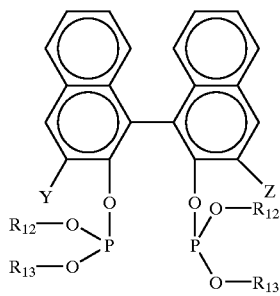

(5)

where Y and Z are substituents other than hydrogen and $R^{12}$ and $R^{13}$ are the same or different substituted monovalent aryl groups and/or any one of $OR^{12}$ and $OR^{13}$ connected to one phosphorus atom forms an —O—$R^{14}$—O-group, where $R^{14}$ is a divalent organic group containing one or two aryl groups.

The substituents Y and Z are preferably organic groups containing at least one carbon atom, more preferably containing 1–20 carbon atoms.

Preferably, Y and Z are individually selected from the group comprising alkyl, aryl, triarylsilyl, trialkylsilyl, carboalkoxy, carboaryloxy, aryloxy, alkoxy, alkylcarbonyl, arylcarbonyl, oxazole, amide, amine or a nitrile.

For Y and Z, the alkyl group is preferably a $C_1$–$C_{10}$ alkyl group, for example methyl, ethyl, propyl, isopropyl, butyl, tert-butyl, isobutyl, pentyl or hexyl. An example of a suitable triarylsilyl group is triphenylsilyl and examples of a suitable trialkylsilyl group are trimethylsilyl and triethylsilyl. Preferred aryl groups have 6 to 20 carbon atoms, for example phenyl, benzyl, tolyl, naphthyl, anthranyl or phenanthryl. Preferred aryloxy groups have 6 to 12 carbon atoms, for example phenoxy. Preferred alkoxy groups have 1 to 20 carbon atoms, for example methoxy, ethoxy, tert-butoxy or isopropoxy. Preferred alkylcarbonyl groups have 2 to 12 carbon atoms, for example methylcarbonyl, tert-butylcarbonyl. Preferred arylcarbonyl groups have 7 to 13 carbon atoms, for example phenylcarbonyl. Preferred amide groups contain a $C_1$–$C_4$ alkyl group and preferred amine groups contain two $C_1$–$C_5$ alkyl groups.

Most preferably, Y and Z are individually a carboalkoxyl or a carboaryloxy group, —$CO_2R$, in which R is a $C_1$–$C_{20}$ alkyl group or a $C_6$–$C_{12}$ aryl group and preferably a $C_1$–$C_8$ alkyl group. Examples of suitable R groups are methyl, ethyl, propyl, isopropyl, n-butyl, tert-butyl, isobutyl, phenyl and tolyl. Even more preferably, Y and Z are both the same carboaryloxy and more preferably the same carboalkoxyl group because the resulting ligands are more easily obtainable.

The 2,2'-dihydroxy-1,1'-binaphtalene bridging group can optionally be further substituted with other groups, for example halogen, for example Cl or F or one of the substituents R which may be present on the bridging group as described above.

$R^{12}$ and $R^{13}$ are preferably the same or different monovalent aryl groups, and more preferably aryl groups with 6 to 20 carbon atoms. It is to be understood that all four $R^{12}$ and $R^{13}$ groups can be different. Preferably all four groups are the same because the resulting ligands are more readily available. Alternatively, $OR^{12}$ and $OR^{13}$ (connected to the same P atom) can form an —O—$R^{14}$—O-group, where $R^{14}$ is a divalent group of 6 to 40 carbon atoms containing one or two aryl groups. Preferably, $R^{12}$ and $R^{13}$ are monovalent aryl groups, for example phenyl, containing at least one group, $R^{15}$, other than hydrogen in an ortho position relative to the oxygen atom, where $R^{15}$ is a $C_1$ to $C_{20}$ alkyl or $C_6$–$C_{20}$ aryl group and preferably a $C_1$–$C_6$ alkyl group. Other preferred monovalent aryl groups for $R^{12}$ and $R^{13}$ are monovalent fused aromatic ring systems with 2 or more rings having 10–20 carbon atoms. $R^{12}$ and $R^{13}$ can optionally be further substituted with for example $C_1$–$C_{10}$ alkyl, $C_6$–$C_{20}$ aryl, $C_1$–$C_{10}$ akoxy or $C_6$–$C_{20}$ aryloxy groups or halogen groups, for example F, Cl or Br or amine groups.

When the aryl groups $R^{12}$ and $R^{13}$ are substituted with at least one $R^{15}$ group at the ortho position relative to the phenolic oxygen atom, a higher linear selectivity is observed when these ligands are used in a hydroformylation process. Examples of these $R^{15}$ groups are methyl, ethyl, propyl, isopropyl, isobutyl, tert-butyl or n-butyl. For $R^{15}$ preferably only one bulky group, having a steric hinderance of isopropyl or greater, is ortho-substituted on the aryl group. When less bulky substituents are used, both ortho positions are preferably substituted with these groups. The preferred $R^{15}$-substituted aryl group for $R^{11}$ and $R^{12}$ is 2-isopropylphenyl or 2-tert-butylphenyl group.

Another preferred class of aryl groups for $R^{12}$ and $R^{13}$ comprises fused aromatic ring systems with 2 or more rings having 10 to 20 carbon atoms which do not necessarily have to be substituted at the ortho position (on the carbon atom adjacent to the carbon atom which is bonded to the oxygen atom in formula (5) with groups other than hydrogen. Examples of such fused aromatic ring systems are phenanthryl, anthryl and naphthyl groups. Preferably 9-phenanthryl or 1-naphthyl groups are used. The aromatic ring systems can optionally be substituted with for example the aforementioned substituents, for example at the positions of the ring systems other than the ortho position described above.

Examples where $R^{12}$ and $R^{13}$ are linked to form divalent groups $R^{14}$ are $C_6$–$C_{25}$ diaryl groups, for example a 2,2'-diphenyldiyl or 2,2'-dinaphtyldiyl group.

These ligands may be prepared using a variety of methods known in the art; see for example descriptions in U.S. Pat. No. 4,769,498; U.S. Pat. No. 4,688,651 and J. Amer. Chem. Soc., 1993, 115, 2066.

The 2,2'-dihydroxy-1,1'-binaphthalene bridged organic bidentate phosphite compounds according to the invention can be prepared with the 3- or 3,3'-substituted 2,2'-dihydroxy-1,1'-binaphthalene bridging compounds. The binaphthol bridging compounds can be prepared by means of procedures as described in Tetrahedron Lett. 1990, 31(3), 413–416 or in J. Am. Chem. Soc. 1954, 76, 296 and Org. Proc. Prep. International, 1991, 23, 200. The phosphite compounds can be prepared by using the process described in the aforementioned U.S. Pat. No. 5,235,113 to couple these binaphthol bridging compounds with phosphorochloridites, $(R^{12}O)(R^{13}O)PCl$, prepared by treating $R^{12}OH$ and/or $R^{13}OH$ with $PCl_3$.

The catalyst system used in the process according to this invention can be prepared by mixing a suitable rhodium or iridium compound with the phosphite ligand, optionally in a suitable solvent, in accordance with well-known complex-forming methods. The solvent will generally be the solvent used in the hydroformylation. Suitable rhodium compounds are for example hydrides, halides, organic acid salts, acetylacetonates, inorganic acid salts, oxides, carbonyl compounds and amine compounds of these metals. Examples of suitable catalyst precursors are $Rh(OAc)_3$, $Rh_2O_3$, $Rh(acac)(CO)_2$, $Rh(CO)_2(DPM)$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$, and $[RhCl(COD)]_2$, (where "acac" is an acetylacetonate group; "Ac" is an acetyl group; "COD" is 1,5-cyclooctadiene; and "Ph" is a phenyl group, DPM is a 2,2,6,6-tetramethyl-3,5-heptanedionate group). However, it should be noted that the rhodium compounds are not necessarily limited to the compounds listed above.

The molar ratio of the multidentate phosphite ligand to rhodium in the hydroformylation reaction mixture and the high boiler purge to be treated is generally from about 0.5 to 100 and preferably from 1 to 10 and most preferably less than 1.2 (mol ligand/mol metal). Preferably the ratio is higher than 1.05. It has been found that in this range the ligand stability during hydroformylation is optimal and the loss of ligand in the high boiler purge according to this invention is minimal.

The invention is therefore also directed to a process to prepare a linear aldehyde, characterized in that the following steps are performed:

(a) hydroformylation of an (internally) unsaturated organic compound in the presence of a catalyst system comprising rhodium and a multidentate organic phosphite ligand, whereby the hydroformylation reaction mixture contains 1–10, preferably 1.05–1.2 mol multidentate phosphite ligand per mol rhodium, (b) separating the linear aldehyde from the reaction mixture obtained in step (a) resulting in a fraction containing the linear aldehyde and a fraction containing the catalyst system and high boiling compounds, (c) purging part of the organic mixture containing the catalyst system and high boiling compounds and recycling the rest to step (a), (d) separating the catalyst system from the high boiling compounds with the process according to the invention, (e) reuse of the catalyst system obtained in step (d) in step (a).

The above described preferences regarding hydroformylation starting compound, conditions and catalyst system also apply here. Step (a) is preferably performed as described in for example U.S. Pat. No. 5,527,950, EP-A-712828 or WO-A-9518089. Step (b) may be performed using any separation technique known to a person skilled in the art. Examples of suit able separation techniques are (vacuum) distillation, crystallisation and extraction using a suitable extraction agent.

The invention will further elucidated by means of the following, non-limiting example s. The rhodium analysis were done by atomic absorption spectroscopy (AAS). The following abbreviations are used: Ph=phenyl, Et=ethyl, OEt=ethoxy, OMe=methoxy, AcAc=acetylacetonate, —Si≡SiO$_2$=linking group SP with three covalent bonds to the silica support, which is represented by $SiO_2$.

EXAMPLE 1

Preparation of Support 1

Preparation of $Ph_2PC_6H_4$-p-Si≡$SiO_2$:

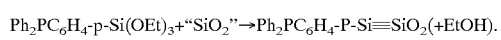

$Ph_2PC_6H_4$-p-Si(OEt)$_3$+"SiO$_2$"→$Ph_2PC_6H_4$-P-Si≡SiO$_2$(+EtOH).

The reaction was carried out under nitrogen in analytical-grade solvents, which were dried before use. 13.5 g of $SiO_2$ (Merck 100) was dried in vacuo at 230° C. for 6 hrs via a cold trap at −80° C. At room temperature and under nitrogen a solution of 3.32 g (7.82 mmol) of $Ph_2PC_6H_4$-p-Si(OEt)$_3$ in 50 ml of hexane was added and the resulting suspension was stirred at room temperature for 72 hrs. Then 50 ml of toluene were added and the temperature was raised to reflux temperature. Within 6 hrs 50 of solvents were distilled off. Then 7 ml (45 mmol) of $Me_3SiOEt$ were added and stirring at reflux temperature was continued for 16 hrs. After cooling, the solid was filtered off and washed four times with 40 ml of toluene and five times with 40 ml of MeOH. Then the product was dried in vacuo at 100° C. for 16 hrs.

Yield: 13.43 g off-white solid. Elemental analyses: 5.36% C, 0.94% H, 0,58% P. Calculated from the P-analysis: 0.187 mmol P/g.

EXAMPLE 2

Preparation of Support 2

Preparation of $Ph_2PC_6H_4$-p-Si≡$SiO_2$:

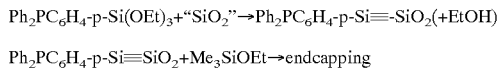

$Ph_2PC_6H_4$-p-Si≡$SiO_2$+$Me_3SiOEt$→endcapping

The reaction was carried out under nitrogen in analytical-grade solvents, which were dried before use. The same procedure, as described for Support 1, was applied to 52 g of $SiO_2$ (Merck 100) and 21.22 g (50 mmol) of $Ph_2PC_6H_4$-p-Si(OEt)$_3$, but now the coupling was performed in 125 ml of toluene at 90° C. for 16 hrs and in the presence of 1 ml of $Et_3N$. Yield: 59.87 g off-white solid. Elemental analyses: 12.41% C, 1.20% H, 1.44% P. Calculated from the P-analysis: capacity 0.465 mmol P/g.

EXAMPLE 3

Preparation of Support 3

Preparation of $Ph_2PC_6H_4$-p-Si(Me)=$SiO_2$:

$Ph_2PC_6H_4$-p-Si(Me) (OEt)$_2$+"$SiO_2$"→$Ph_2PC_6H_4$-p-Si(Me)=$SiO_2$(+EtOH)

$Ph_2PC_6H_4$-p-Si(Me)=$SiO_2$+$Me_3SiOEt$→endcapping

The reaction was carried out under nitrogen in analytical-grade solvents, which were dried before use. 167 g of $SiO_2$ (Merck 100) was dried in vacuo at 240° C. for 8 hrs via a cold trap at −80° C. At room temperature and under nitrogen a solution of 38.04 g (96.4 mmol) of $Ph_2PC_6H_4$-p-Si(Me)(OEt)$_2$ in 600 ml of hexane was added and the resulting suspension was stirred at room temperature for 72 hrs. Then 300 ml of toluene were added and the temperature was raised to reflux temperature. Within 3.5 hrs 150 ml of solvents were distilled off. Then 80 ml (ca. 500 mmol) of $Me_3SiOEt$ were added and stirring at reflux temperature was continued for 18 hrs. After cooling, the solid was filtered off and washed two times with 300 ml of hexane. Thereafter, the solid was extracted in a Soxhlet apparatus for 8 hrs with toluene and for 8 hrs with methanol, respectively. Then the product was dried in vacuo at 100° C. for 24 hrs. Yield: 163.6 g colourless solid. Elemental analyses: 6.38% C, 0.95% H, 0.40% P. Calculated from the P-analysis: capacity 0.129 mmol P/g.

EXAMPLE 4

Preparation of Support 4

Preparation of $Ph_2PC_6H_4$-p-Si(Me)=$SiO_2$:

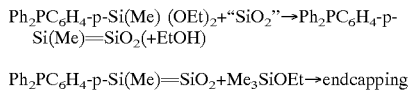

$Ph_2PC_6H_4$-p-Si(Me)=$SiO_2$+$Me_3SiOEt$→endcapping

The reaction was carried out under nitrogen in analytical-grade solvents, which were dried before use. The same procedure, as described for Support 3, was applied to 99.82 g of $SiO_2$ (Davisil 646) and 37.8 g (95.8 mmol) of $Ph_2PC_6H_4$-p-Si(Me) (oEt)$_2$, but now the coupling was performed in 320 ml of toluene at 90° C. for 21 hrs and in the presence of 2 ml of $Et_3N$. Yield: 106.06 g colourless solid. Elemental analyses: 9.21% C, 0.82% H, 0.93% P. Calculated from the P-analysis: capacity 0.300 mmol P/g.

EXAMPLE 5

Preparation of Support 5

Preparation of $Ph_2PC_6H_4$-p-Si(Me)$_2$—O—$SiO_2$:

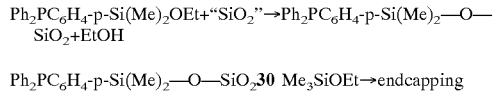

$Ph_2PC_6H_4$-p-Si(Me)$_2$—O—$SiO_2$30 $Me_3SiOEt$→endcapping

The reaction was carried out under nitrogen in analytical-grade solvents, which were dried before use. 65 g of $SiO_2$ (Alfa 22629) was dried in vacuo at 240° C. for 8 hrs via a cold trap at −80° C. At room temperature and under nitrogen a solution of 11.38 g (31.22 mmol) of $Ph_2PC_6H_4$-p-Si(Me)$_2$OEt in 200 ml of hexane was added and the resulting suspension was stirred at room temperature for 22 hrs. Then 150 ml of toluene was added and the temperature was raised to reflux temperature. Within 3.5 hrs 150 ml of solvents were distilled off. Then 25 g (212 mmol) of $Me_3SiOEt$ were added and stirring at reflux temperature was continued for 18 hrs. After cooling, the solid was filtered off and washed three times with 50 ml of toluene and five times with 50 ml of MeOH. The product was then dried in vacuo at 100° C. for 24 hrs. Yield: 59.88 g off-white solid. Elemental analyses: 2.64% C, 0.81% H, 0.15% P. Calculated from the P-analysis: capacity 0.049 mmol P/g.

EXAMPLE 6

Preparation of Support 6

Preparation of $Ph_2PC_6H_4$-p-Si(Me)$_2$—O—$SiO_2$:

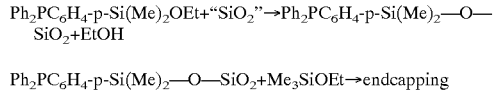

$Ph_2PC_6H_4$-p-Si(Me)$_2$—O—$SiO_2$+$Me_3SiOEt$→endcapping

The reaction was carried out under nitrogen in analytical-grade solvents, which were dried before use. The same procedure, as described for Support 5, was applied to 52 g of $SiO_2$ (Merck 100) and 9.05 g (24.8 mmol) of $Ph_2PC_6H_4$-p-Si(Me)$_2$OEt, but now the coupling was performed in 175 ml of toluene at 90° C. for 16 hrs and in the presence of 1 ml of $Et_3N$. Yield: 59.49 g colourless solid. Elemental analyses: 9.67% C, 1.21% H, 0.95% P. Calculated from the P-analysis: capacity 0.306 mmol P/g.

EXAMPLE 7

Preparation of Support 7

Preparation of $Ph_2P(CH_2)_8Si$≡$SiO_2$:

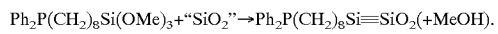

The reaction was carried out under nitrogen in analytical-grade solvents, which were dried before use.

55.17 g of $SiO_2$ (Alfa 22629) was dried in vacuo at 230° C. for 8 hrs via a cold trap at −80° C. At room temperature and under nitrogen a solution of 13.8 g (33.1 mmol) of Ph$_2$P(CH$_2$)$_8$Si(OMe)$_3$ in 200 ml of hexane was added and the resulting suspension was stirred at room temperature for 65 hrs. Then 100 ml of toluene was added and the temperature was raised to reflux temperature. Within 3.5 hrs. 150 ml of solvents were distilled off. Stirring at reflux temperature was continued overnight. After cooling, the solid was filtered off and washed four times with 50 ml of toluene and six times with 50 ml of MeOH. The product was then dried in vacuo at 100° C. for 24 hrs. Yield: 59.23 g off white solid. 31p NMR in CDCl$_3$ (slurry): (P)ca. −17 ppm (br). Elemental analyses: 12.380% C, 1.56% H, 1.53% P. Calculated from the P-analysis: 0.49 mmol P/g.

EXAMPLE 8 (Support 7)

Recovery of Rhodium Complex from High Boiler Hydroformylation Purge

A typical high-boiler residue was obtained from a hydroformylation experiment in which methyl-3-pentenoate is hydroformylated to methyl-5-formylvalerate in a continuous manner. The catalyst employed for this hydroformylation consisted of Rh(AcAc) (CO)$_2$, a bidentate phosphite ligand as is shown below:

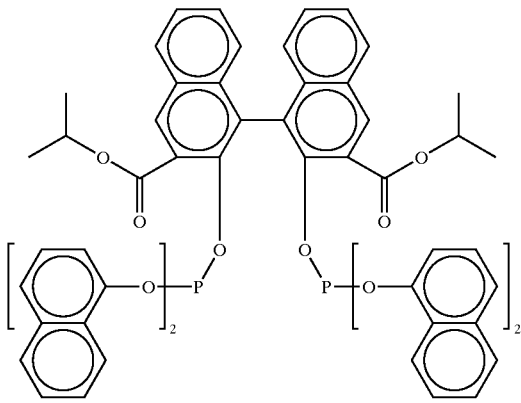

triortho-tolyl-phosphine added as an anti-oxydant and a carboxylic acid (mostly mono-methyladipate). Performing such a hydroformylation reaction in a continuous way for 250 hours, in which constantly fresh make-up ligand was added and continuously 100 g per hour of methyl-3-pentenoate was added at 95° C. under 0.5 MPa pressure (CO/H$_2$=1) and the products were removed by distillation yielded in the end 1000 g of a residue. In this residue all the initial added rhodium was still present and at least 8% high-boilers were build-up. This residue mixture was used for rhodium recovery experiments.

From the high boiler mixture described above, 20 ml was taken and put under nitrogen atmosphere. The rhodium concentration of this mixture was 360 ppm (AAS). To this was added 4.25 g of Support 7 which contained 0.49 mmol P/g, so the Rh/P-molar ratio is 1/30. This mixture was stirred for six hours at 20° C. after which period a sample was taken from the liquid for analysis. This sample contained 12 ppm Rh so an efficiency of 96% adsorption was achieved.

EXAMPLE 9 (Support 7)

Example 8 was repeated but instead of 4.25 g of the phosphorous containing silica only 0.71 g was used so the Rh/P molar ratio was decreased to 1/5. This mixture was stirred for six h at 20° C. and after that a sample from the liquid was taken and it contained 62 ppm Rh, so an adsorption efficiency of 82% was reached. Increasing the temperature to 95° C. for 7 hours gave no increase in adsorption efficiency.

EXAMPLE 10 (Support 7)

Another 20 ml of the high-boiler purge mixture of example 8 was taken and diluted with 40 ml of toluene. This mixture, containing 120 ppm Rh, was put under 1 MPa CO/H$_2$=1 for 2 h at 95° C., after which the pressure was released. Then 4.25 g of the support 7 (Rh/P=1/30) was added and stirring at 20° C. under nitrogen was continued for 20 h. After this time a sample was taken from the liquid and analysis revealed 0.7 ppm Rh. This means that Rh is adsorbed with a 99% efficiency.

EXAMPLE 11 (Support 7)

The silica of example 10 was isolated after the Rhodium was adsorped and it was washed with toluene. Then this silica was put into an autoclave and 60 ml of methyl-5-formylvalerate was added. This mixture was heated to 95° C. under 8 MPa CO/H$_2$ for 3 h after which a liquid sample was taken. This contained 65 ppm Rh which means Rhodium could be desorped with an efficiency of 33% in one step.

EXAMPLE 12 (Support 1)

25.1 mg Rh(AcAC) (CO)$_2$, 511 mg (5 eq) of the bidentate phosphite ligand used in Example 8, 290 mg tris-ortho-tolylphosphine and 5 ml methyl-3-pentenoate were dissolved in 75 ml toluene under nitrogen in an autoclave. Then 1.0 MPa CO/H$_2$ was applied and the temperature was raised to 95° C. while stirring at 1100 rpm for 3 hours. After this time the hydroformylation of the methyl-3-pentenoate was almost complete, giving 83% selectivity to methyl-5-formylvalerate. This mixture was cooled of to room temperature and the pressure was released. The autoclave was purged two times with 5 bar N$_2$ after which the pressure was set at 0.1 MPa nitrogen. From this mixure a liquid sample (1 ml) was taken which was analysed for Rh: 113 ppm. Next 1.3 g of support 1 made in example 1 was added (P/Rh= 2.5/1) and stirring was continued for 5 hours after which a 1 ml sample was taken from the liquid and analysed for Rh: 23 ppm. This means that 79% of all the rhodium was adsorped on the silica. Next a CO/H$_2$ pressure was applied of 5.0 MPa after which the temperature was increased to 60° C. After 3 hours a sample was taken and the Rh was found to be 114 ppm. This means that almost quantitative desorption of rhodium had taken place.

EXAMPLE 13 (Support 7)

Example 12 was repeated but instead of 1.3 g of support 1, 0.83 g of support 7 (made in example 7) (P/Rh=1/5) was added to the liquid sample (1 ml) containing 113 ppm Rh. After stirring for 5 hours a 1 ml sample was taken from the liquid and analysed for Rh: 14.3 ppm. This means that 87.3% of all the rhodium was adsorbed on the silica. Next a CO/H$_2$ pressure of 8 MPa was applied after which the temperature was increased to 95° C. After 3 hours of stirring a sample was taken and the rhodium content of the liquid was found to be 78 ppm. This means that the adsorbed rhodium could be desorbed with an efficiency of 62% in one step.

EXAMPLE 14 (Support 3)

Example 12 was repeated but instead of 1.3 g of support 1, 1.1 g of support 3 was added to the liquid sample (1 ml) containing 113 ppm Rh.

The silica was then isolated, washed twice with 40 ml of toluene and dried in vacuo at 100° C. for 18 hours. Yield: 1.05 g of a light yellow solid. Rhodium analysis: 0.065 mmol Rh/g. In an autoclave and under nitrogen, 0.26 g of this solid was suspensed in 60 ml of methyl-5-formylvalerate, containing 0.15 g of the bidentate ligand used in Example 8. The autoclave was purged 10 times with 1.0 MPa $CO/H_2$. Then 5.0 MPa $CO/H_2$ was applied and the temperature was raised to 95° C. while stirring at 1100 rpm. Stirring was continued for 3 hours. A 1 ml sample was taken from the liquid and analysed for Rh: 28.7 ppm. This means that almost quantitative desorption of rhodium had taken place. The mixture was cooled off to room temperature and the pressure was released. 15 ml of the high boiler mixture, as described in Example 8 was then added. The autoclave was purged ten times with 0,2 MPa nitrogen while stirring. Stirring was continued for 2 hours, whereafter the solid was isolated, washed two times with 40 ml of toluene and dried in vacuo for 4 hours. Yield: 0.2 g light of a yellow solid. Rhodium analysis: 0.060 mmol Rh/g. This means that reloading of the silica was achieved for 92.3%, as compared with the first loading. In an autoclave and under nitrogen, 0.14 g of this solid was suspended in 45 ml of methyl-5-formylvalerate, containing 0.08 g of the bidentate ligand used in Example 8. The autoclave was purged 10 times with 1.0 MPa $CO/H_2$. Then 5.0 MPa $CO/H_2$ was applied and the temperature was raised to 95° C. while stirring at 1100 rpm. Stirring was continued for 3 hours. A 1 ml sample was taken from the liquid and analysed for Rh: 17.5 ppm. This means that the adsorbed rhodium could now be desorbed with an efficiency of 90.5% in one step. Example 14 illustrates that the process of the invention regenerates the support for direct re-use.

EXAMPLE 15 (Support 5)

30 ml of a toluene based stock solution containing 139 ppm Rh as Rh(acac) $(CO)_2$, 6 eq (to Rh) of the bidentate ligand used in Example 8, 10 eq (to Rh) of tris-ortho-tolylphosphine and 2 ml of methyl-3-pentenoate were diluted with 50 ml of toluene and placed in an autoclave under nitrogen. Then 1.0 MPa $CO/H_2$ was applied and the temperature was raised to 95° C. while stirring at 1100 rpm for 3 hours. After this time the hydroformylation of the methyl-3-pentenoate was almost complete, giving 83% selectivity to methyl-5-formylvalerate. This mixture was cooled to room temperature and the pressure was released. The autoclave was purged 6 times with 0,5 MPa nitrogen after which the pressure was set at 0.1 MPa nitrogen. Next 4.3 g of the support made in Example 5 was added (P/Rh= 5.2/1) and stirring was continued for 3 hours after which time a 1 ml sample was taken from the liquid and analysed for Rh: 6.9 ppm. This means that 87% of all of the rhodium was adsorbed on the silica. After 20 hours of stirring the liquid was analysed again for Rh: 5.0 ppm. This means that now 91% of all of the rhodium was adsorbed on the silica. stirring for another 15.5 hours at 45° C., followed by analysis of the liquid, showed the adsorption to be 93% (4.0 ppm Rh). Next a $CO/H_2$ pressure was applied of 5.0 MPa after which the temperature was increased to 95° C. After 3 hours of stirring a sample was taken and the Rh was found to be 51 ppm. This means that the adsorbed rhodium could be desorbed with an efficiency of 76% in one step.

EXAMPLE 16 (Support 2)

Recovery of Rhodium Complex from High Boiler Hydroformylation Purge

Example 8 was repeated, but instead of 20 ml of the high boiler mixture 24.8 ml of a high boiler mixture were placed in an autoclave under nitrogen. The rhodium concentration of the mixture was 196 ppm. Then, while stirring, the solution was heated to 95° C. under 1 MPa $CO/H_2$ for 2 hours. The pressure was released after cooling to room temperature. Then 3 g of support 2 made in Example 2 was added (P/Rh=30/1), whereafter the autoclave was purged 10 times with 0, 5 MPa nitrogen while stirring. Next, the pressure was set at 0,2 MPa nitrogen and stirring was continued for 2 hours. After that period, a sample was taken from the liquid for analysis. This sample contained 40.8 ppm rhodium, so an efficiency of 83.2% adsorption was achieved in one step.

EXAMPLE 17 (Support 6)

Recovery of Rhodium Complex from High Boiler Hydroformylation Purge

Example 8 was repeated, but instead of 20 ml of the high boiler mixture 8 ml of a high boiler mixture containing 75 ppm rhodium, were added under nitrogen to 4 g of support 6 made in Example 6 (P/Rh=215/1). The resulting mixture was stirred for 0.5 hour. Then a sample of the liquid was taken, filtered and analysed for Rh: 15.3 ppm. This means that 79.6% of all of the rhodium was adsorbed on the silica.

EXAMPLE 18 (Support 4)

Recovery of Rhodium Complex from High Boiler Hydroformylation Purge

Example 8 was repeated, but instead of 20 ml of the high boiler mixture 40 ml of a high boiler mixture containing 75 ppm rhodium, were placed in an autoclave under nitrogen. While stirring, the autoclave was put under 1 MPa $CO/H_2$ and at 90° C. for 2 hours. The pressure was released after cooling to room temperature. Next, under nitrogen, 14 ml of the mixture were taken out of the autoclave and added to 6 g of support 4 made in Example 4 (P/Rh=176/1). The resulting mixture was stirred for 1 hour. Then a sample of the liquid was taken, filtered and analysed for Rh: 6.5 ppm. This means that 91.3% of all of the rhodium was adsorbed on the silica.

EXAMPLE 19 (Support 5)

Recovery of Rhodium Complex from High Boiler Hydroformylation Purge

Example 8 was repeated, but instead of 20 ml of the high boiler mixture 20 ml of a high boiler mixture were diluted with 60 ml of toluene and placed in an autoclave under nitrogen. The rhodium concentration of this mixture was 50 ppm. Then 0.2 g (5.1 eq to Rh) of the bidentate ligand used in Example 3 was added and the resulting solution was heated to 95° C. under 1 MPa $CO/H_2$ for 2 hours. The pressure was released after cooling to room temperature. Then 8.0 g of support 5 made in Example 5 was added (P/Rh=10.3/1), whereafter the autoclave was purged 5 times with 0,5 MPa nitrogen while stirring. Then the pressure was set at 0,2 MPa nitrogen. Stirring was continued for 20 hours after which period a sample was taken from the liquid for analysis. This sample contained 12.3 ppm rhodium, so an efficiency of 76% adsorption was achieved in one step. Then all liquid was pressed out the autoclave via a filter and the silica was washed with 70 ml of toluene, which was also pressed out. Then 70 ml of methyl-5-formylvalerate were added, together with 0.26 g (6 eq to Rh) of the bidentate ligand used in Example 3. This mixture was heated to 90° C.

under 8 MPa CO/H₂ f or 9.5 hours after which period a sample of the liquid w as taken for analysis. This sample contained 23 ppm Rh which means that rhodium could be desorbed with an efficiency of 58% in one step.

EXAMPLE 20 (Support 2)

Recovery of Rhodium Complex from High Boiler Hydroformylation Purge

Example 8 was repeated, but instead of 20 ml of the high boiler mixture 45 ml of a high boiler mixture were placed in an autoclave under nitrogen. The rhodium concentration of th is mixture was 204 ppmn Then 99.2 mg (1 eq to Rh) of the bidentate ligand used in Example 3 was added and the resulting solution was heated to 95° C. under 1 MPa CO/H₂ for 2 hours. The pressure was released after cooling to room temperature. Then 1.96 g of support 2 made in Example 2 was added (P/Rh=10/1), whereafter The autoclave was purged 5 times with 0,5 MPa nitrogen while stirring. Then the pressure was set at 0,2 MPa nitrogen. Stirring was continued for 3 hours after which period a sample was taken from the liquid for analysis. This sample contained 70 ppm rhodium, so an efficiency of 67.6% adsorption was achieved in one step. Then a solution of 0.40 g (4 eq to Rh) of the bidentate ligand used in Example 3 in toluene was added. Next, while stirring, a CO/H₂ pressure was applied of 5 MPa after which the temperature was increased to 90° C. Stirring was continued for 3 hours after which period a sample was taken and the Rh concentration was found to be 152 ppm. This means that the adsorbed rhodium could be desorbed with an efficiency of 60.2% in one step.

What is claimed is:

1. Process for separation a group 8–10 metal/phosphite ligand complex from an organic liquid mixture, comprising:

(1) contacting the organic liquid with a support having bonded thereto an organophosphine ligand and separating the organic mixture poor in group 8–10 metal/phosphite ligand complex, (2) contacting the thus obtained loaded support with an organic solvent and carbon monoxide and separating the thus obtained organic solvent rich in group 8–10 metal/phosphite ligand complex, and (3) reusing the support obtained in step (2) in step (1).

2. Process according to claim 1, wherein the group 8–10 metal is rhodium.

3. Process according to anyone of claims 1–2, wherein step (2) is performed in the presence of hydrogen.

4. Process according to claim 1–2, wherein step (2) is performed by contacting the loaded support with an organic solvent saturated with CO or CO/H₂.

5. Process according to claim 1–2, wherein the support having bonded thereto an organophosphine ligand is represented by the formula (1) or (2):

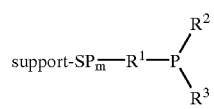

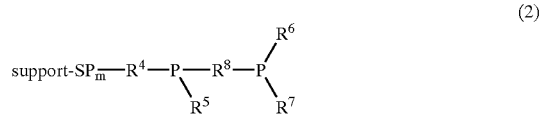

wherein m=0 or 1, SP is a linking group, $R^2$, $R^3$, $R^5$, $R^6$ and $R^7$ are the same or different optionally substituted hydrocarbon groups containing 1–30 carbon atoms and $R^1$, $R^4$ and $R^8$ are divelent organic bridging groups having 1–30 carbon atoms.

6. Process according to claim 5, wherein the organophosphine ligand is a monodentate phosphine according to formula (1).

7. Process according to claim 6, wherein $R^1$, $R^2$, $R^3$ are optionally substituted phenyl groups.

8. Process according to claim 1–2, wherein the support is an inorganic support.

9. Process according to claim 8, wherein the inorganic support is silica and SP is a—Si(R')(R")—group wherein R' and/or R" is an alkyl, alkoxy, aryl or aryloxy group and/or R' and/or R" is a covalent bond to the silica support.

10. Process according to claim 2, wherein the organic liquid mixture also contains high boiling hydroformylation compounds.

11. Process for preparation of a linear aldehyde, comprising:

(a) hydroformylating an internally unsaturated organic compound in the presence of a catalytic system comprising rhodium and a multidentate organic phospite ligand, whereby the hydroformylation reaction mixture contains 1–10 mol multidentate phosphite ligand per mole of rhodium, (b) separating the linear aldehyde from the reaction mixture obtained in step (a) resulting in a fraction containing the linear aldehyde and a fraction containing the catalyst system and high boiling compounds, (c) purging the fraction containing the catalyst system and high boiling compounds and recycling the rest to step (a), (d) separating the catalyst system from the high boiling compounds with the process according to anyone of claims 1–2, (e) reusing the catalyst system obtained in step (d) in step (a).

12. Process according to claim 3 wherein step (2) is performed by contacting the loaded support with an organic solvent which has been saturated with CO or CO/H₂.

* * * * *

UNITED STATES PATENT AND TRADEMARK OFFICE
CERTIFICATE OF CORRECTION

PATENT NO. : 6,455,740 B1
DATED : September 24, 2002
INVENTOR(S) : Broeders et al.

It is certified that error appears in the above-identified patent and that said Letters Patent is hereby corrected as shown below:

<u>Title page,</u>
Item [73], Assignee, please add the following Assignee:
-- E.I. Dupont de Nemours and Company --.

Signed and Sealed this

First Day of April, 2003

JAMES E. ROGAN
*Director of the United States Patent and Trademark Office*